(12) United States Patent
Keshav et al.

(10) Patent No.: US 9,663,505 B2
(45) Date of Patent: May 30, 2017

(54) PROCESS FOR THE PREPARATION OF RIVAROXABAN

(71) Applicant: Glenmark Pharmaceuticals Limited, Mumbai (IN)

(72) Inventors: Shrikant Prabhakar Keshav, Navi Mumbai (IN); Sanjay Shashikant Bhise, Mumbai (IN); Hemant Harishchandra Kamble, Mumbai (IN); Ganesh Chaudhari, Ahemdnagar (IN); Deepak Subhash Patil, Thane (IN); Srinivas Reddy Sanikommu, Andhra Pradesh (IN); Kumar Hari Bhushan, Gurgaon (IN); Shekhar Bhaskar Bhirud, Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/780,138

(22) PCT Filed: Mar. 21, 2014

(86) PCT No.: PCT/IB2014/060028
§ 371 (c)(1),
(2) Date: Sep. 25, 2015

(87) PCT Pub. No.: WO2014/155259
PCT Pub. Date: Oct. 2, 2014

(65) Prior Publication Data
US 2016/0052919 A1    Feb. 25, 2016

(30) Foreign Application Priority Data

Mar. 25, 2013 (IN) .......................... 1113/MUM/2013

(51) Int. Cl.
*C07D 413/14* (2006.01)
*C07D 413/12* (2006.01)

(52) U.S. Cl.
CPC ......... *C07D 413/14* (2013.01); *C07D 413/12* (2013.01)

(58) Field of Classification Search
None
See application file for complete search history.

(56) References Cited

U.S. PATENT DOCUMENTS

| | | |
|---|---|---|
| 7,157,456 B2 | 1/2007 | Straub et al. |
| 7,351,823 B2 | 4/2008 | Berwe et al. |
| 7,592,339 B2 | 9/2009 | Straub et al. |
| 7,598,378 B2 | 10/2009 | Thomas et al. |
| 7,816,355 B1 | 10/2010 | Bodhuri et al. |
| 8,106,192 B2 | 1/2012 | Thomas |
| 2011/0288294 A1 | 11/2011 | Nonnenmacher et al. |

FOREIGN PATENT DOCUMENTS

| | | |
|---|---|---|
| CN | 102250076 A | 11/2011 |
| WO | 2011012321 A1 | 2/2011 |
| WO | 2011080341 A1 | 7/2011 |
| WO | 2011098501 A1 | 8/2011 |
| WO | 2012035057 A2 | 3/2012 |
| WO | 2012051692 A1 | 4/2012 |
| WO | 2012159992 A1 | 11/2012 |
| WO | 2013121436 A2 | 8/2013 |

*Primary Examiner* — Samantha Shterengarts
(74) *Attorney, Agent, or Firm* — Ryan, Mason & Lewis, LLP

(57) ABSTRACT

Disclosed is a process for the preparation of rivaroxaban and purifying rivaroxaban.

11 Claims, No Drawings

PROCESS FOR THE PREPARATION OF RIVAROXABAN

PRIORITY

This application claims priority under 35 U.S.C. §371 to International Application No. PCT/IB2014/060028, filed Mar. 21, 2014 which claims the benefit under 35 U.S.C. §119 to Indian Provisional Application No. 1113/MUM/2013, filed Mar. 25, 2013, the contents of which are incorporated by reference herein.

FIELD OF THE INVENTION

The present invention relates to a novel process for the preparation of rivaroxaban.

BACKGROUND OF THE INVENTION

Rivaroxaban, chemically known as 5-chloro-N({(5S)-2-oxo-3-[4-(3-oxo-4-morpholinyl)phenyl]-1,3oxazolidin-5-yl}methyl)-2-thiophenecarboxamide, has the following structural Formula I:

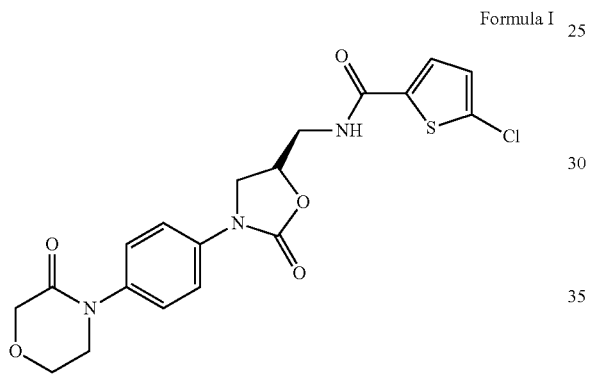

Formula I

Rivaroxaban, an inhibitor of clotting factor Xa, is marketed in the United States under the trade name XARELTO® as tablets in the dosage strength of 10 mg, 15 mg and 20 mg.

Rivaroxaban can be used for the prevention and treatment of various thromboembolic disease, in particular of deep vein thrombosis (DVT), pulmonary embolism (PE), myocardial infract, angina pectoris, reocclusions and restenoses after angioplasty or aortocoronary bypass, cerebral stroke, transitory ischemic attacks, and peripheral arterial occlusive diseases.

U.S. Pat. No. 7,157,456 discloses a process for the preparation of rivaroxaban by reacting a compound of Formula II

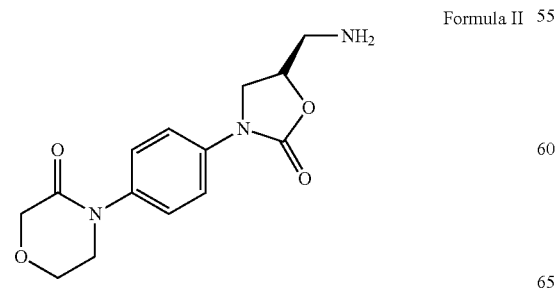

Formula II with 5-chlorothiophene-2-carbonyl chloride.

U.S. Pat. Nos. 7,351,823, 7,598,378, 7,816,355 and 8,106,192 also disclose process for rivaroxaban.

United States Patent Publication US2011/288294 and PCT Patent Publication WO2011/012321, WO2011/080341, WO 2011/098501, and WO2012/051692 also disclose process for rivaroxaban.

There is a need for an improved process for the preparation of rivaroxaban, which avoids the formation of isomeric and other process-related impurities, while affording the desired rivaroxaban product with high yield and purity.

We have now developed a novel process for the preparation of rivaroxaban which is simple, reproducible, robust and well suited on commercial scale.

SUMMARY OF THE INVENTION

The present invention relates to process for the preparation of rivaroxaban, a compound of Formula I,

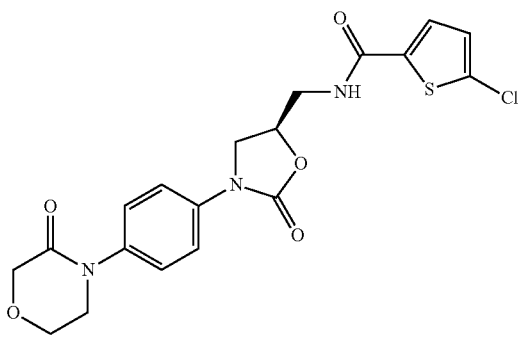

Formula I comprising the steps of a) contacting a compound of Formula II or salt thereof

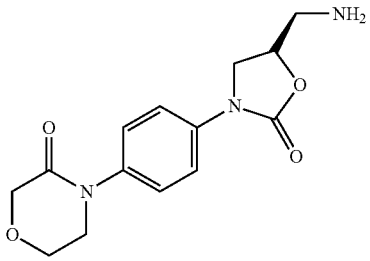

Formula II with an oxidizing agent to form a first reaction mixture;
b) then contacting the first reaction mixture with a compound of formula VIII,

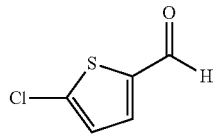

Formula VIII to form a second reaction mixture; and
c) isolating a compound of formula I from the second reaction mixture The present invention relates to process for purifying rivaroxaban, a compound of Formula I, comprising:

a) providing a solution of rivaroxaban in a mixture of alcohol solvent and halogenated hydrocarbon solvent or their aqueous mixtures;
b) precipitating the solid from the solution; and
c) isolating the pure rivaroxaban, a compound of Formula I.

DETAILED DESCRIPTION OF THE INVENTION

The present invention is directed to an improved process for the preparation of rivaroxaban.

Present health care reforms and legislation lead to evolving and increasingly rigorous requirements demanded of drug manufacturers. There is need for improved processes for the preparation of rivaroxaban and its intermediates, which would circumvent the formation of process related impurities, while ensuring a target rivaroxaban product with optimum yield and purity.

In one embodiment, the present invention relates to process for the preparation of rivaroxaban, a compound of Formula I, Formula I

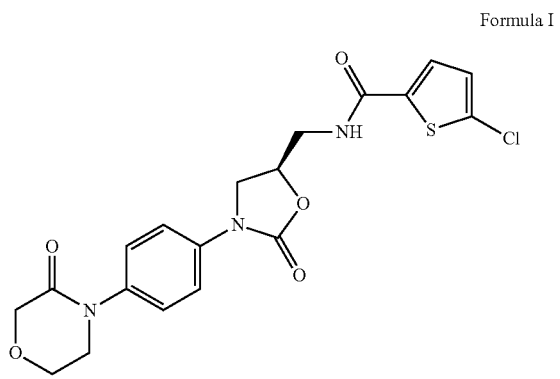 [SMILES: O=C(NC[C@@H]1CN(c2ccc(N3CCOCC3=O)cc2)C(=O)O1)c1ccc(Cl)s1]

comprising the step of a) contacting a compound of Formula II or salt thereof,

Formula II

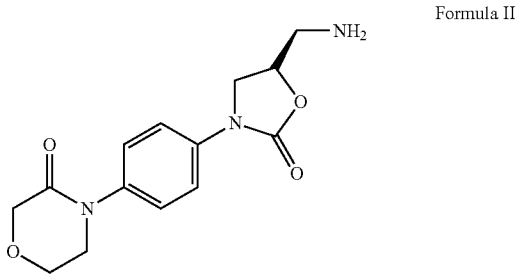

with an oxidizing agent to form a first reaction mixture;
b) then contacting the first reaction mixture with a compound of formula VIII, Formula VIII

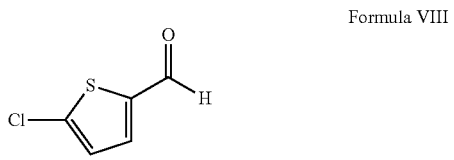

to form a second reaction mixture; and
c) isolating a compound of formula I from the second reaction mixture.

In step a), the oxidizing agent is selected from the group consisting of tert-butyl hydroperoxide, benzoyl peroxide, cumene hydro peroxide, and the like. Preferably, tert-butyl hydroperoxide.

In step a), the amount of oxidizing agent is from about 1 mole to about 3 moles per mole of the compound of formula II or salt. Preferably, from about 1 mole to about 2 moles per mole of the compound of formula II or salt.

In one embodiment, the compound of formula II or salt thereof is contacted with an oxidizing agent in presence of a base to form a first reaction mixture.

A suitable base may be selected from an inorganic base or organic base. The inorganic base may be selected from alkali metal or alkaline earth metal hydroxide, such as sodium hydroxide, potassium hydroxide, calcium hydroxide, lithium hydroxide, alkali metal alkoxide such as sodium methoxide, potassium methoxide, alkali metal or alkaline earth metal carbonates or bicarbonates such as sodium carbonate, potassium carbonate, calcium carbonate, sodium bicarbonate, potassium bicarbonate, calcium bicarbonate, cesium carbonate and the like. Preferably, calcium carbonate.

The organic base may be selected from the group consisting of organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like.

In one embodiment, the compound of formula II or salt thereof is contacted with an oxidizing agent in presence of a catalyst to form a first reaction mixture.

A suitable catalyst may be selected from copper iodide (CuI), copper bromide (CuBr), sodium iodide (NaI), sodium bromide (NaBr), lithium bromide (LiBr), silver iodate ($AgIO_3$), sodium iodate ($NaIO_3$) and the like or mixtures thereof. Preferably copper iodide (CuI) and silver iodate ($AgIO_3$).

The catalyst can be used from about 0.01 mole to about 0.05 moles per mole of the compound of formula II or salt thereof, preferably about 0.01 mole to about 0.005 moles per mole of the compound of formula II or salt thereof.

In one embodiment, the compound of formula II or salt thereof is contacted with an oxidizing agent in presence of a base and a catalyst to form a first reaction mixture.

The base and catalyst are same as described above.

In one embodiment, the compound of formula II or salt thereof is contacted with an oxidizing agent in presence of a solvent to form a first reaction mixture.

The solvent may be selected from nitriles such as acetonitrile, propionitrile, butyronitrile, isobutyronitrile, benzonitrile and the like; esters such as ethyl acetate, propyl acetate, isopropyl acetate, butyl acetate, and like; alcohols such as methanol, ethanol, n-propanol, 2-propanol, tert-butanol, n-butanol and the like; ethers such as diethyl ether, diisopropyl ether, tetrahydrofuran, dioxane and the like, water or mixture thereof. Preferably, acetonitrile and ethyl acetate.

In one embodiment, the compound of formula II or salt thereof is contacted with an oxidizing agent in presence of copper iodide, silver iodate and calcium carbonate in nitrile solvent to generate a first reaction mixture.

In one embodiment, the first reaction mixture may be stirred for a period of about 10 minutes to 60 minutes.

In step b), the first reaction mixture generated is contacted with compound of formula VIII.

The compound of formula VIII is added to first reaction mixture at a temperature in the range of about 25° C. to 50° C. and the reaction mass was stirred for a period of about 2 to 6 hours to generate a second reaction mixture.

The stirring may be carried out at a temperature range of about 30-50° C.

The compound of formula I is isolated from the second reaction mixture by workup.

In one embodiment, the compound I is isolated by filtration from second reaction mixture.

In one embodiment, prior to filtration the second reaction mixture is treated with an acidic medium and then subjected to filtration to isolate compound of formula I.

In one embodiment, the compound of formula I thus obtained is treated with formic acid followed by addition of water to precipitate the compound of formula I and followed by isolating the compound I by filtration.

In one embodiment, the above reaction is carried out at about 5° C. to about 80° C.

Surprisingly, it has been found that the process of the present invention involving preparation of rivaroxaban, a compound of formula I, by contacting compound of formula II or salt thereof with an oxidizing agent and then adding compound of formula VIII, has a significant advantage of obtaining rivaroxaban with high purity (HPLC Purity: 90%) for pharmaceutical use. In contrast if the oxidizing agent is added after the reaction of compound of formula II or salt thereof with a compound of formula VIII, then the rivaroxaban obtained has a purity to the extent of about 70% only and is contaminated with impurities.

Without wishing to be bound by theory it is believed that the process of the present invention involving contacting a compound of formula II or salt thereof with an oxidizing agent followed by addition of compound of formula VIII proceeds through oxidative amidation to form rivaroxaban and not via compound of formula XI, as demonstrated by HPLC.

Formula XI

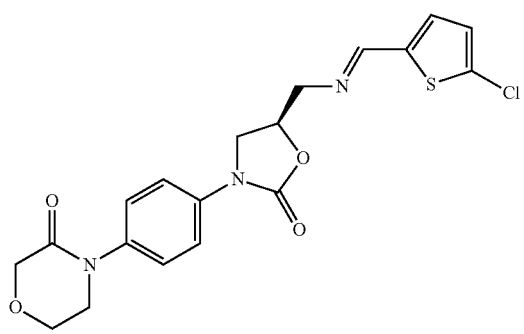

In one embodiment, the present invention provides rivaroxaban a compound of Formula I, obtained by the process described above, which is free of compound of formula XI.

In one embodiment, the present invention provides a process for the preparation of rivaroxaban, a compound of Formula I, comprising simultaneous addition of a compound of formula II, an oxidizing agent and a compound of formula VIII.

In one embodiment, compound I is treated with DMF and the solution obtained is passed through neutral alumina column, followed by addition of water to eluted DMF solution to precipitate the compound I and followed by isolating the pure compound I by filtration to obtain compound I with HPLC purity of 99.5%.

In one embodiment, the present invention provides process for purifying rivaroxaban, a compound of Formula I, comprising:
a) providing a solution of rivaroxaban in a mixture of alcohol solvent and halogenated hydrocarbon solvent or their aqueous mixtures;
b) precipitating the solid from the solution; and
c) isolating the pure rivaroxaban, a compound of Formula I.

In step a), the solvent may be selected from alcohol such as methanol, ethanol, n-propanol, 2-propanol, tert-butanol, n-butanol and the like; halogenated hydrocarbon solvent such as methylene chlorie (MDC), ethylene chloride (EDC), chloroform and the like, water or mixture thereof. Preferably mixture of methanol and methylene chloride (MDC).

In one embodiment, in step a), the reaction mixture is heated and stirred at about 35° C. to about 55° C.

In step b), precipitation of the solid from the solution is achieved by distillation of solvent at about 40° C. to about 70° C. and by cooling the solution to room temperature.

In step c), isolated rivaroxaban is dried at about 45° C. to about 75° C., preferably at about 50° C. to about 60° C.

In one embodiment, the present invention provides rivaroxaban wherein the level of compound of formula IX less than 0.15%, w/w preferably below detection limit (BDL) w/w relative to the amount of rivaroxaban as determined by HPLC.

In one embodiment, the present invention provides rivaroxaban wherein the level of compound of formula X is less than 0.15% w/w, preferably less than 0.05% w/w relative to the amount of rivaroxaban as determined by HPLC.

In one embodiment, the present invention provides rivaroxaban a compound of Formula I, obtained by the processes herein described, which is substantially free of compound of formula XI.

Formula XI

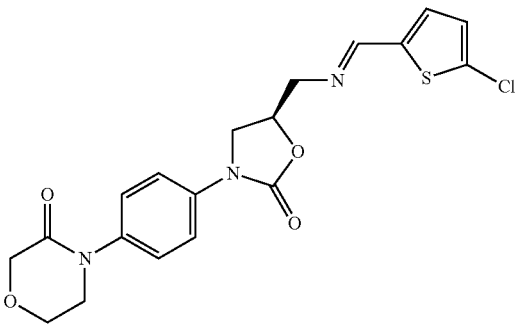

Formula XI

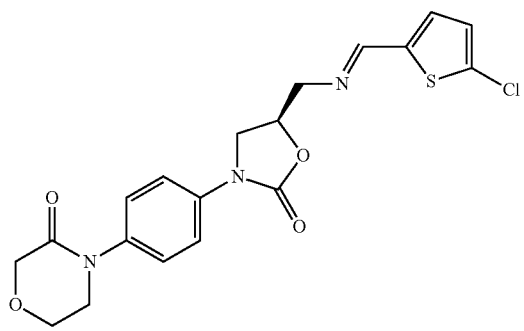

The term substantially free means that rivaroxaban prepared in accordance with present invention contains less than about 0.15% w/w, preferably less than about 0.05% w/w, and more preferably below detection limit of compound XI as measured by HPLC.

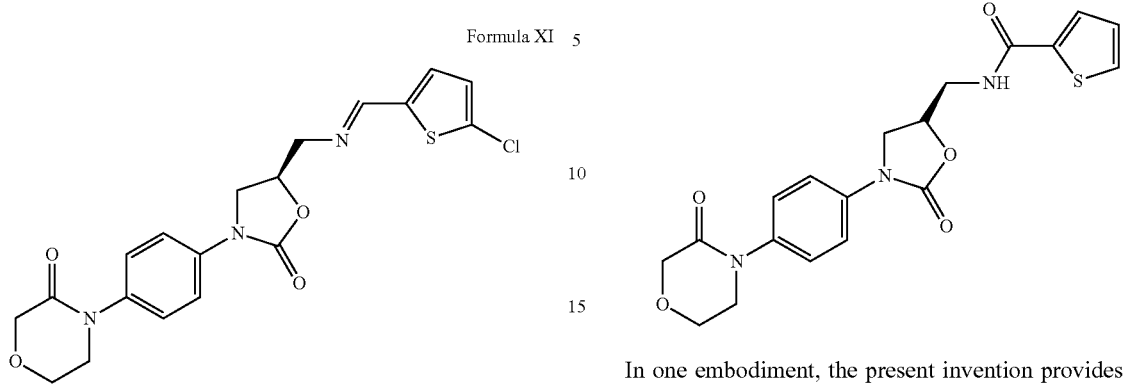

Formula XI

In one embodiment, the present invention provides rivaroxaban a compound of Formula I, free of compound of formula XI.

Formula XI

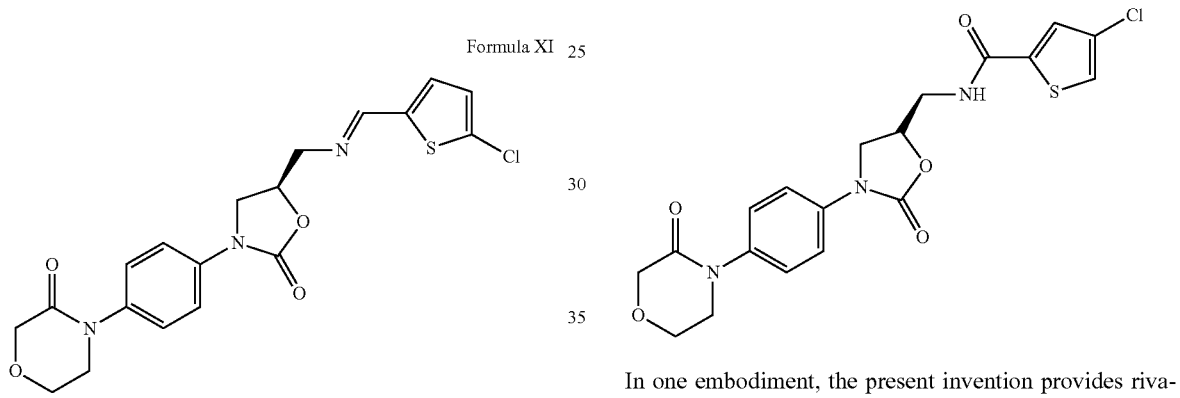

Reaction mixture is analysed by HPLC using GL-Science, Inertsil ODS 3V column at 243 nm. Buffer used is 0.01 M ammonium acetate in water. Mobile phase is Methanol:Acetonitrile (60:40) with flow rate 1.0 ml/min. compound of formula XI is eluted at 33.0 min. (RRT 1.10).

In one embodiment, the present invention provides rivaroxaban wherein the level of compound of formula IX is less than 0.15%, w/w relative to the amount of rivaroxaban as determined by HPLC.

Formula IX

In one embodiment, the present invention provides rivaroxaban wherein the level of compound of formula X is less than 0.15%, w/w relative to the amount of rivaroxaban as determined by HPLC.

Formula X

In one embodiment, the present invention provides rivaroxaban wherein the level of compound of formula XII is less than 0.15%, w/w relative to the amount of rivaroxaban as determined by HPLC.

Formula XII

In one embodiment, the present invention provides rivaroxaban wherein the level of compound of formula XII is less than 0.15%, w/w relative to the amount of rivaroxaban as determined by HPLC.

Formula XIII

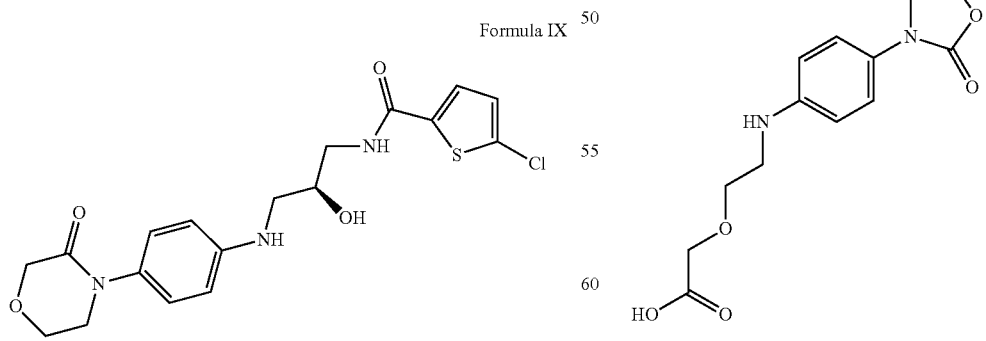

In one embodiment, the present invention provides rivaroxaban wherein the level of compound of formula XII is less than 0.15% w/w, preferably below detection limit relative to the amount of rivaroxaban as determined by HPLC.

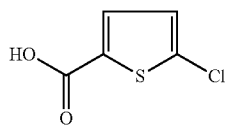

Formula XIV

In one embodiment, the present invention provides rivaroxaban a compound of Formula I, wherein the level of (R)-rivaroxaban impurity is present less than 0.15% w/w relative to the amount of rivaroxaban as determined by chiral HPLC.

In one embodiment, the present invention provides rivaroxaban a compound of Formula I, obtained by the processes herein described, having purity more than about 99.6% as measured by High Performance Liquid Chromatography (HPLC).

In one embodiment, the present invention provides rivaroxaban, wherein level of one or more compounds of formula II, IV, V, VIII, IX, X, XII, XIII and XIV is level of less than 0.15% w/w relative to the amount of rivaroxaban as determined by HPLC and (R)-rivaroxaban less than 0.15% w/w relative to the amount of rivaroxaban as determined by chiral-HPLC.

In one embodiment the present invention provides rivaroxaban, compound of formula I, having bulk density of 0.312 g/cc.

In one embodiment the present invention provides rivaroxaban, compound of formula I, having taped density of 0.47 g/cc.

In one embodiment the present invention provides rivaroxaban, compound of formula I having specific surface area of about 0.31 m²/g.

In one embodiment, the present invention provides modification I of rivaroxaban.

In one embodiment, the present invention provides rivaroxaban a compound of Formula I, obtained by the processes herein described, is rivaroxaban modification I, characterized by X-ray powder diffraction (XRPD) and near infra-red (NIR) spectra.

In one embodiment the present invention provides a process for preparing rivaroxaban compound of formula I in the modification I characterized by X-ray powder diffraction having peaks expressed as 2θ values at about 8.9, 14.3, 16.5, 17.4, 18.0, 19.5, 19.9, 21.7, 22.5, 23.3, 24.7, 25.6, 26.4, 26.6, 30.0, and 31.8±0.2.

In one embodiment the present invention provides rivaroxaban a compound of Formula I, obtained by the processes herein described, having a $D_{90}$ particle size of about 103 microns, $D_{50}$ particle size of about 55 microns and $D_{10}$ particle size of about 15 microns.

In one embodiment, the present invention provides micronized rivaroxaban a compound of Formula I, obtained by the processes herein described, having a $D_{90}$ particle size of about 65 microns, $D_{50}$ particle size of about 35 microns and $D_{10}$ particle size of about 12 microns.

In one embodiment, the present invention relates to process for the preparation of compound of Formula VIII,

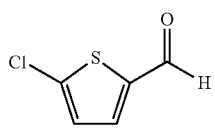

Formula VIII comprising: reacting 2-chlorothiophene with phosphorous oxychloride.

In one embodiment, 2-chlorothiophene reacted with phosphorous oxychloride in presence of a solvent.

The solvent may be selected from dimethyl formamide (DMF), acetonitrile, toluene, and the like. Preferably, dimethyl formamide (DMF).

In one embodiment, reaction of 2-chlorothiophene with phosphorous oxychloride is carried out at about 40° C.-65° C., preferably at about 50° C.-55° C.

In one embodiment, the present invention relates to process for the preparation of rivaroxaban, a compound of Formula I,

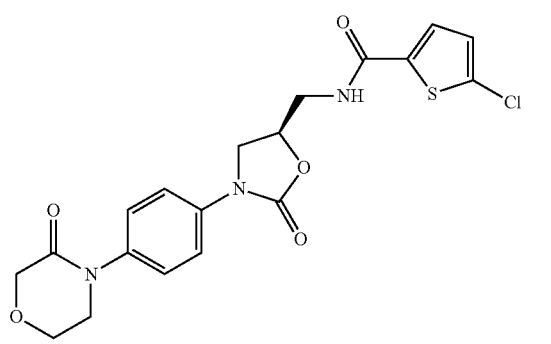

Formula I comprising: reacting a compound of Formula II

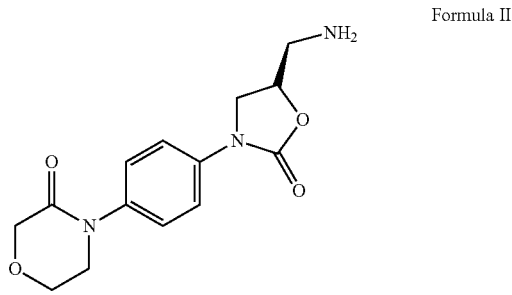

Formula II with a compound of formula III,

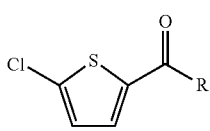

Formula III wherein R is selected from

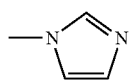

or —OSO2R¹, wherein R¹ is selected from the group consisting of $C_1$-$C_6$ alkyl, alkylaryl, aryl and substituted aryl wherein the substituent on the aryl is present at one or more positions on the aryl ring, selected from the group consisting of halogen, nitro, $C_1$-$C_6$ alkyl, and $C_1$-$C_6$ alkoxy.

The term "alkyl" as used herein includes a straight or branched chain hydrocarbon containing from 1 to 6 carbon atoms. Representative examples of alkyl include, but are not limited to, methyl, ethyl, n-propyl, isopropyl, n-butyl, sec-butyl, tert-butyl, n-pentyl, isopentyl, neopentyl, n-hexyl.

The term "aryl" as used herein, refers to aromatic ring systems, which may include fused rings. Representative examples of aryl include, but are not limited to, phenyl, and naphthyl, anthracenyl, phenant.

The term "alkylaryl" as used herein, refers to an aryl group, as defined herein, appended to the parent molecular moiety through an alkyl group, as defined herein. Representative examples of alkylaryl include, but are not limited to, benzyl, 2-phenylethyl, 3-phenylpropyl, and 2-naphth-2-ylethyl.

The term "alkoxy" as used refers to an alkyl group, as defined herein, appended to the parent molecular moiety through an oxygen atom. Representative examples of alkyloxy include, but are not limited to, methoxy, ethoxy, propoxy, butoxy.

The term "substituted aryl" as used refers to substituent on the aryl is present at one or more positions on the aryl ring, selected from the group consisting of halogen such as chloro, bromo, iodo; nitro; $C_1$-$C_6$ alkyl wherein alkyl refers to methyl, ethyl, n-propyl, isopropyl, n-butyl, sec-butyl, tert-butyl, n-pentyl, isopentyl, neopentyl, n-hexyl and $C_1$-$C_6$ alkoxy wherein alkoxy refers to methoxy, ethoxy, propoxy, butoxy.

In one embodiment, the present invention provides a process for preparing a compound of formula I wherein R is a compound of formula

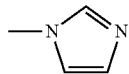

or p-toluene sulfonyl, methane sulphonyl, trifluoromethane sulphonyl, benzene sulphonyl and the like.

In one embodiment, the present invention relates to process for the preparation of rivaroxaban, a compound of Formula I, Formula I

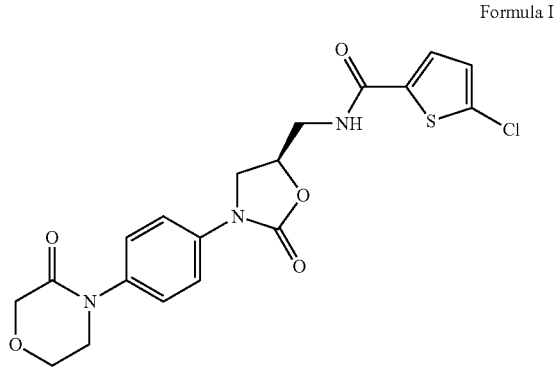 [SMILES: O=C(NC[C@@H]1CN(c2ccc(N3CCOCC3=O)cc2)C(=O)O1)c1ccc(Cl)s1]

comprising reacting a compound of Formula II

Formula II

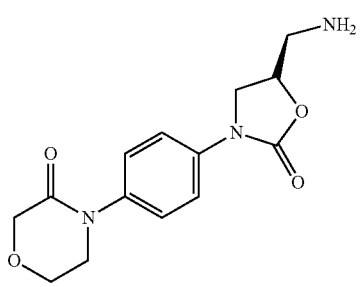

with a compound of formula IIIa,

Formula IIIa

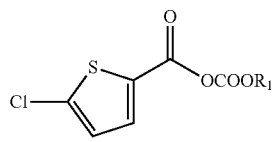

wherein $R_1$ is $C_1$-$C_6$ alkyl group such as methyl, ethyl, n-propyl, isopropyl, butyl, pentyl or hexyl.

In one embodiment, in the above process a compound of formula II, is reacted with a compound of formula III or formula IIIa in the presence of a suitable solvent.

A suitable solvent may be selected from, but is not limited to esters such as ethyl acetate, propyl acetate, butyl acetate; ketones such as acetone, methyl ethyl ketone, methyl isobutyl ketone, 2-propanone; hydrocarbon such as toluene, benzene, xylene, cyclohexane; halogenated hydrocarbons such as methylene dichloride, ethylene dichloride, chloroform, carbon tetrachloride, alcohols such as methanol, ethanol, n-propanol, 2-propanol, tert-butanol, n-butanol; ethers such as diethyl ether, di-isopropyl ether, tetrahydrofuran, dioxane, water or mixtures thereof. Preferably, the solvent is methylene dichloride and tetrahydrofuran.

The reaction may be optionally carried out in presence of coupling reagent selected from the group consisting of 1-hydroxybenzotriazole (HOBT), 1, 8-Diazabicyclo[5.4.0]undec-7-ene (DBU), carbonyldiimidazole (CDI), diisopropylylcarbodiimide (DIC), dicyclohexylcarbodiimide (DCC) and the like or mixtures thereof.

The reaction may be carried out in presence or absence of base. A suitable base may be selected from organic or inorganic base. The inorganic base may be selected from the group consisting of hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like. The organic base may be selected from triethyl amine, trimethyl amine, diisopropyl ethylamine, dimethyl amino pyridine, picoline, dimethyl amino pyridine and pyridine. Preferably, the base is triethyl amine.

In one embodiment, the present invention provides a process for preparing a compound of formula I wherein R is a compound of formula,

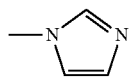

the reaction is carried out in absence of a base.

In one embodiment, present invention provides a process for the preparation of compound of formula III (wherein R is

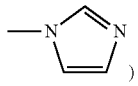
)

comprising reacting 5-chloro-2-thiophenecarboxylic acid with 1,1-carbonyl diimidazole.

In one embodiment, present invention provides a process for the preparation of compound of formula III (wherein R is p-toluene sulfonyl) comprising reacting 5-chloro-2-thiophenecarboxylic acid with p-toluene sulfonyl chloride.

In one embodiment, present invention provides a process for the preparation of compound of formula IIIa (wherein R is OCOOCH$_3$, OCOOC$_2$H$_5$) comprising reacting 5-chloro-2-thiophenecarboxylic acid with methyl chloroformate or ethyl chloroformate.

In one embodiment, the present invention provides a process for the preparation of compound of formula III or IIIa, comprising not isolating a compound of formula III or formula IIIa prepared from the reaction mixture; and adding a compound of formula II to the compound of formula III or formula IIIa.

In one embodiment, the present invention provides a process for the preparation of compound of formula III or IIIA, comprising isolating a compound of formula III or formula Ma prepared; then optionally purifying, for example, by crystallization using suitable organic solvents and/or subjecting to column chromatography etc; and then treating with compound of formula II to synthesize the compound of Formula I.

In one embodiment, the present invention provides a compound of formula IIIb.

Formula IIIb

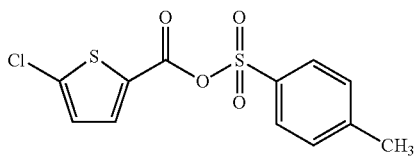

In one embodiment, the present invention provides a compound of formula IIIb and its use as an intermediate in the synthesis of rivaroxaban.

In one embodiment, the present invention provides a process for the preparation of compound of formula II or salt thereof, Formula II

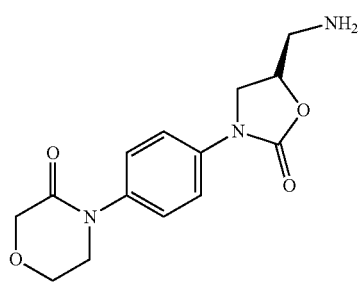

comprising reacting a compound of Formula IV

Formula IV

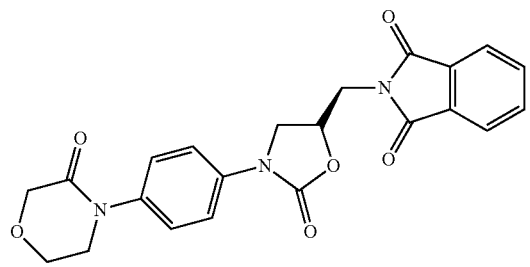

with a suitable solvent and a base.

A suitable solvent may be selected from, but is not limited to alcohols such as methanol, ethanol, n-propanol, 2-propanol, isopropanol, tert-butanol, n-butanol; hydrocarbon such as toluene, benzene, xylene, cyclohexane; halogenated hydrocarbons such as methylene dichloride, ethylene dichloride; esters such as ethyl acetate, propyl acetate, butyl acetate; ketones such as acetone, methyl ethyl ketone, methyl isobutyl ketone, 2-propanone; ethers such as diethyl ether, di-isopropyl ether, tetrahydrofuran; water or mixtures thereof. Preferably, the solvent is methanol, water.

A suitable base may be selected from organic or inorganic base. The inorganic base may be selected from the group consisting of hydroxides such as sodium hydroxide, potassium hydroxide, calcium hydroxide; aqueous ammonia; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like. The organic base may be selected from methyl amine, triethyl amine, trimethyl amine, diisopropyl ethylamine, dimethyl amino pyridine, picoline, dimethyl amino pyridine and pyridine or aqueous mixtures thereof. Preferably the reaction is carried out in the presence of aqueous methyl amine.

In one embodiment, the above reaction may be carried out in the presence of an acid.

The acid that can be used in the reaction may be selected from the group consisting of hydrochloric acid, acetic acid, phosphoric acid, trifluoracetic acid, trifluoromethane sulfonic acid, methane sulfonic acid, nitric acid, sulfuric acid or the mixtures thereof In one embodiment, compound of formula II may be crystallized/purified by solvent selected from alcohols, esters, ethers, ketones, nitriles, hydrocarbons or mixtures thereof.

In one embodiment, the present invention provides a process for the preparation of compound of formula IV, Formula IV

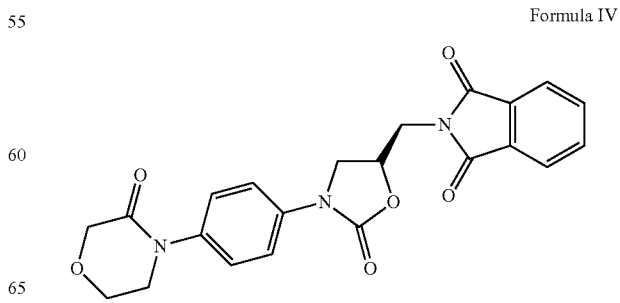

comprising reacting a compound of Formula V

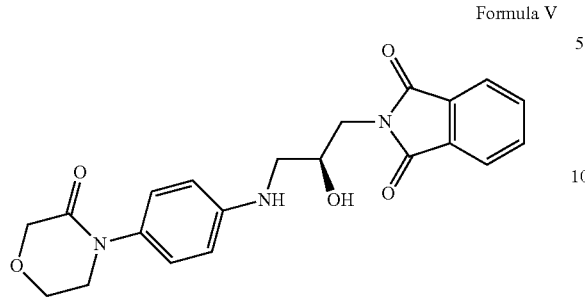

Formula V with 1,1'-carbonyl diimidazole in presence of suitable solvent.

A suitable solvent may be selected from, ethers such as diethyl ether, di-isopropyl ether, tetrahydrofuran; hydrocarbon such as toluene, benzene, xylene, cyclohexane; halogenated hydrocarbons such as methylene dichloride, ethylene dichloride; esters such as ethyl acetate, isopropyl acetate, butyl acetate; ketones such as acetone, methyl ethyl ketone, methyl isobutyl ketone, 2-propanone; acetonitrile or mixtures thereof.

In one embodiment, the present invention provides a process for purifying compound of formula IV from solvent may be selected from alcohol such as methanol, ethanol, propanol and like; hydrocarbon solvent such as cyclohexane, MDC, EDC, chloroform and the like; ketone such as acetone, methyl isobutyl ketone (MIBK), propanone and the like; nitrile such as acetonitrile, propionitrile and the like; ether such as tetrahydrofuran (THF), diethyl ether, dimethyl formamide, dimethyl acetamide, nitrobenzene, water or mixture thereof. Preferably methanol and nitrobenzene.

In one embodiment, the present invention provides a process for the preparation of compound of formula V, comprising reacting a compound of Formula VI,

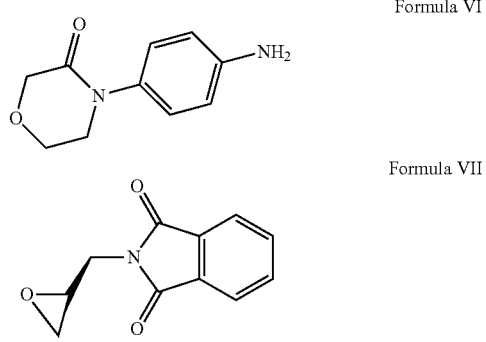

Formula VI

Formula VII with a compound of formula VII, in presence of suitable solvent.

A suitable solvent may be selected from alcohols such as methanol, ethanol, n-propanol, 2-propanol, tert-butanol, n-butanol; halogenated hydrocarbons such as methylene dichloride, ethylene dichloride; esters such as ethyl acetate, propyl acetate, butyl acetate; ketones such as acetone, methyl ethyl ketone, methyl isobutyl ketone, 2-propanone; ethers such as diethyl ether, di-isopropyl ether, tetrahydrofuran; acetonitrile, water or mixtures thereof.

In one embodiment, the present invention provides a process for the preparation of compound of formula V, comprising reacting a compound of Formula VI,

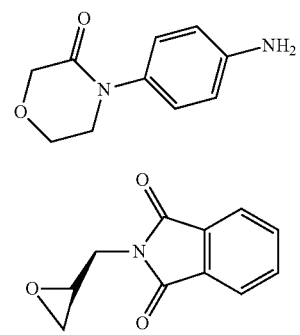

Formula VI

Formula VII with a compound of formula VII, in presence of water.

After completion of the reaction, the desired compounds can be isolated from the reaction mixture by conventional means known in the art. For example, the working-up of reaction mixtures follows customary isolation techniques, known to the organic chemists skilled in the norms of the art and steps, e.g. selected from the group comprising but not limited to extraction, neutralization, crystallization, chromatography, evaporation, drying, filtration, centrifugation and the like. Preferably, crystallization.

In one embodiment, the present invention provides a process for purifying rivaroxaban comprising:
a) providing a solution of rivaroxaban in a solvent or a mixture of solvents or their aqueous mixtures; b) precipitating the solid from the solution; and c) recovering the pure rivaroxaban.

The solvent or mixture of solvents is selected from a C2-C5 nitrile, a C2-C6 ester, C3-C5 ketone, C1-C5 alcohol, cyclic ether, hydrocarbon solvents and their halogenated derivatives. The C2-C5 nitrile include acetonitrile, propionitrile and the like; C2-C6 ester include ethyl acetate, isopropyl acetate, isobutyl acetate, t-butyl acetate and the like; C3-C5 ketone include acetone, methyl ethyl ketone, ethyl methyl ketone and the like; C1-C5 alcohol include methanol, ethanol, isopropanol, isobutanol, 2-butanol; cyclic ether include tetrahydrofuran (THF), dioxane and the like; hydrocarbon solvents and halogenated derivatives thereof may include pentane, n-hexane, heptane, cyclohexane, petroleum ether, m-, o-, or p-xylene, dichloromethane (MDC), chloroform, carbon tetrachloride, 1,2-dichloroethane; polar solvent such as dimethylformamide (DMF), dimethylsulfoxide, dimethyl acetamide, water or mixtures thereof.

The processes, herein described, for the preparation of rivaroxaban are simple, eco-friendly, inexpensive, reproducible, robust and well suited on industrial scale. While the present invention has been described in terms of its specific embodiments, certain modifications and equivalents will be apparent to those skilled in the art and are intended to be included within the scope of the present invention.

EXAMPLES

Example 1: Preparation of (2-[(2R)-2-hydroxy-3-{[4-(3-oxomorpholin-4-yl)phenyl]amino}propyl]-1H-isoindole-1,3(2H)-dione (Formula V)

In a clean round bottom flask, 100 gm of 4-(4-aminophenyl) morpholin-3-one, 126.9 gm of 2-[(2S)-oxiran-2-ylmethyl]-1H-isoindole-1,3(2H)-drone and 2 liter water were charged. The reaction mixture was heated to a temperature of about 55-60° C. and maintained for about 15 hours. The reaction mass was cooled to about room temperature and stirred for about one hour, filtered, washed with water and dried in air oven at about 50° C.-55° C. to yield 200 gm of titled compound.

Example 2: Preparation of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 200 gm of 2-[(2S)-2-hydroxy-3-{[4-(3-oxomorpholin-4-yl) phenyl] amino}propyl]-1H-isoindole-1,3(2H)-dione, 10 gm of 4-dimethyl amino pyridine, 164 gm of 1,1'-carbonyl diimidazole (CDI) and 3 liter of tetrahydrofuran (THF) were charged. The reaction mixture was heated to about 55-60° C. and stirred for about 12 hours. A second lot of 164 gm of 1,1-carbonyl diimidazole (CDI) was charged and the reaction mass was maintained for about 12 hours. The reaction mass was then cooled to about 0° C. to 5° C. and stirred for about 2 hours, filtered, washed with chilled THF and dried in air oven at about 50° C.-55° C. to yield 162 gm of titled compound.

Example 3: Preparation of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 100 gm of 2-[(2S)-2-hydroxy-3-{[4-(3-oxomorpholin-4-yl)phenyl] amino}propyl]-1H-isoindole-1,3(2H)-dione, 5 gm of 4-dimethyl amino pyridine, 82 gm of 1,1'-carbonyl diimidazole (CDI) and 2.5 liter of toluene were charged. The reaction mixture was heated to about 55-60° C. and stirred for about 12 hours. A second lot of 82 gm of 1,1-carbonyl diimidazole (CDI) was charged and the reaction mass was maintained for about 12 hours. The reaction mass was then cooled to about 0° C. to 5° C. and stirred for about 2 hours, filtered, washed with chilled toluene and dried in air oven at about 50° C.-55° C. to yield 90 gm of titled compound.

Example 4: Preparation of Compound of Formula IIIb

In a clean round bottom flask, 30 gm of 5-chlorothiophene-2-carboxylic acid, 300 ml of methylene dichloride (MDC) were charged and stirred at about room temperature then 38.71 gm of p-toluene sulfonyl chloride was added. The reaction mass was cooled to about 0° C.-5° C. and triethylamine (TEA) was added drop wise and stirred for about 2-3 hours at about the same temperature. 300 ml of 5% sodium bicarbonate solution was added to the reaction mass and stirred. The organic layer was separated and washed with 5% sodium bicarbonate solution followed by water. MDC layer was distilled off under vacuum and degassed for about one hour to get a thick solid mass. 60 ml of n-hexane was added to the obtained mass and stirred for about one hour, filtered and dried to yield 32 gm of titled compound.

Example 5: Preparation of Compound of Formula IIIb

In a clean round bottom flask, 30 gm of 5-chlorothiophene-2-carboxylic acid, 300 ml of toluene were charged and stirred at about room temperature then 38.71 gm of p-toluene sulfonyl chloride was added. The reaction mass was cooled to about 0° C.-5° C. and potassium carbonate was added. The reaction mass was stirred for about 10-12 hours at about room temperature, filtered and toluene layer was washed with 5% sodium bicarbonate solution followed by water. The toluene layer was distilled off under vacuum and degassed for about one hour to get a thick solid mass. 60 ml of cyclohexane was added to obtained mass and stirred for about one hour, filtered and dried to yield 32 gm of titled compound.

Example 6: Preparation of (4-{4-[(5S)-5-(amino methyl)-2-oxo-1,3-oxazolidin-3-yl] phenyl}morpholin-3-one (Formula II)

In a clean round bottom flask, 100 gm of (2-({(5S)-2-oxo-3-[4-(3-oxomorpholin-4-yl)phenyl]-1,3-oxazolidin-5-yl}methyl)-1H-isoindole-1,3(2H)-dione), 1 liter of methanol and 223.6 gm of 40% aq. methyl amine solution were charged at about room temperature. The reaction mixture was heated to about 60° C.-65° C. for about 2 hours. The reaction mixture was then cooled to about 40° C. and distilled off completely under vacuum. The residue was dissolved in methylene dichloride (MDC) and washed with sodium chloride solution. The methylene dichloride (MDC) layer was dried over sodium sulphate and MDC was distilled off under vacuum. The solid thus obtained was stirred in ethyl acetate, filtered, washed with ethyl acetate and dried in air oven at about 50° C.-55° C. to yield 65 gm of titled compound.

Example 7: Preparation of 4-{4-[(5S)-5-(amino methyl)-2-oxo-1,3-oxazolidin-3-yl] phenyl}morpholin-3-one (Formula II)

In a clean round bottom flask, 10 gm of (2-({(5S)-2-oxo-3-[4-(3-oxomorpholin-4-yl)phenyl]-1,3-oxazolidin-5-yl}methyl)-1H-isoindole-1,3(2H)-dione, 30 ml of water and 22.42 gm of 40% aq. methyl amine solution were charged. The reaction mixture was heated to about 60° C.-65° C., maintained for about 3 hours and distilled off under vacuum below about 50° C., the residue stripped with 50 ml of toluene. To obtained residue 200 ml MDC added and stirred. MDC layer dried over sodium sulphate and distilled off under vacuum below 45° C. to yield titled compound.

Example 8: Preparation of 4-{4-[(5S)-5-(amino methyl)-2-oxo-1,3-oxazolidin-3-yl] phenyl}morpholin-3-one (Formula II)

In a clean round bottom flask, 10 gm of (2-({(5S)-2-oxo-3-[4-(3-oxomorpholin-4-yl)phenyl]-1,3-oxazolidin-5-yl}methyl)-1H-isoindole-1,3(2H)-dione, 30 ml of water and 22.42 gm of 40% aq. methyl amine solution were charged. The reaction mixture was heated to about 60° C.-65° C., maintained for about 3 hours. The reaction mixture was cooled to room temperature and saturated with sodium chloride and extracted with acetonitrile. The organic layer was then washed with saturated sodium chloride solution. The organic layer was distilled off completely under vacuum. The solid obtained was stirred with 20 ml of ethyl acetate at about room temperature, filtered, washed with ethyl acetate and dried in air oven at about 50° C.-55° C. to yield titled compound.

Example 9: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 15 gm of 5-Chloro thiophene-2-carboxylic acid, 150 ml of tetrahydrofuran (THF)

and 18 gm of 1,1-carbonyl diimidazole (CDI) were charged and stirred for about one hour. To this reaction mixture 12.5 gm of 1-Hydroxybenzotriazole (HOBT), 40.3 gm of 4-{4-[(5S)-5-(amino methyl)-2-oxo-1,3-oxazolidin-3-yl]phenyl}morpholin-3-one were charged. The reaction mixture was stirred overnight, filtered and washed with THF. The wet cake obtained was washed with 5% sodium bicarbonate solution and water and dried in air oven at about 50° C.-60° C. to yield 32 gm to yield titled compound. Purity: 96.42% by HPLC.

Example 10: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 0.557 gm of 5-chloro thiophene-2-carboxylic acid, 5 ml of THF and 0.557 gm of 1,1-carbonyldiimidazole (CDI) were charged at room temperature and stirred for about one hour. 1.5 gm of 4-{4-[(5S)-5-(amino methyl)-2-oxo-1,3-oxazolidin-3-yl]phenyl}morpholin-3-one was added to reaction mixture and stirred overnight at room temperature, filtered, washed with THF and dried in air oven at about 50° C.-55° C. to yield titled compound.

Example 11: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 0.5 gm of 5-Chloro thiophene-2-carboxylic acid and 10 ml of tetrahydrofuran (THF) were charged under nitrogen atmosphere and then 0.61 gm of 1,1-carbonyl diimidazole (CDI) was added and stirred for about 2 hours. To this reaction mixture 0.47 gm of 1, 8-Diazabicyclo[5.4.0]undec-7-ene (DBU), 0.90 gm of 4-{4-[(5S)-5-(amino methyl)-2-oxo-1,3-oxazolidin-3-yl]phenyl}morpholin-3-one were charged and stirred overnight at room temperature. The reaction mixture was quenched with water and extracted with ethyl acetate. The ethyl acetate layer was washed with 5% HCl solution and 5% sodium bicarbonate solution, followed by saturated sodium chloride solution. The ethyl acetate layer was dried over sodium sulphate and distilled off to yield titled compound.

Example 12: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 2 gm of 5-Chloro thiophene-2-carboxylic acid and 20 ml of tetrahydrofuran (THF) were charged and cooled to about 0° C.-10° C. To this reaction mass 1.9 gm of triethyl amine (TEA), 2.60 gm of p-toluene sulphonyl chloride (PTSC) were added and stirred for about 20-60 minutes and then 5.4 gms of 4-{4-[(5S)-5-(amino methyl)-2-oxo-1,3-oxazolidin-3-yl]phenyl}morpholin-3-one was added and stirred for about 5 hours at about 0° C.-10° C. To this reaction mass, water was added and the temperature was raised to room temperature and further stirred for about 10-30 minutes, filtered, washed with water and dried in an air oven at about 50° C.-55° C. to yield 3.3 gm of titled compound. Purity: 97.15% by HPLC Example 13: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 5 gm of 4-{4-[(5S)-5-(amino methyl)-2-oxo-1,3-oxazolidin-3-yl]phenyl}morpholin-3-one, 50 ml of tetrahydrofuran (THF) and 5.4 gm of compound of formula IIIb were charged at room temperature. The reaction mass was stirred for about 12-15 hours at about room temperature and 100 ml of water was added and further stirred for about one hour. The reaction mass was filtered, washed with water and dried in air oven at about 50° C.-55° C. to yield 4.8 gm of titled compound.

Example 14: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 5 gm of 4-{4-[(5S)-5-(amino methyl)-2-oxo-1,3-oxazolidin-3-yl]phenyl}morpholin-3-one, 50 ml of dimethylformamide (DMF) and 5.4 gm of compound of formula IIIb were charged at room temperature. The reaction mass was stirred for about 5-6 hours at about room temperature and 100 ml of water was added and further stirred for about one hour. The reaction mass was filtered, washed with water and dried in air oven at about 50° C.-55° C. to yield 4.8 gm of titled compound.

Example 15: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask 2 gm of 5-chloro thiophene-2-carboxylic acid and 20 ml of methylene dichloride (MDC) were charged and reaction mixture was cooled to about −5° C. to −10° C. and then 1.5 gm of triethyl amine (YEA) was added and stirred for about 5-20 minutes. To this reaction mass 1.5 gm of ethylchloroformate or methyl chloroformate was added and stirred for about one hour and then 3.6 gm of 4-{4-[(5S)-5-(amino methyl)-2-oxo-1,3-oxazolidin-3-yl]phenyl}morpholin-3-one was added and further stirred for about one hour at about −5° C. to −10° C. The temperature of reaction mass was raised to room temperature and quenched with ice-cold water. The organic layer was washed with 5% HCl solution and 5% sodium bicarbonate solution, followed by saturated sodium chloride solution, dried over sodium sulphate, distilled off and degassed to titled compound. Purity: 95.27% by HPLC.

Example 16: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 1 gm of 5-Chloro thiophene-2-carboxylic acid and 20 ml of methylene dichloride (MDC) were charged and reaction mixture was cooled to about −5° C. to −10° C. and then 1.4 gm of triethyl amine (YEA) was added and stirred for about 5-20 minutes. To this reaction mass 0.74 gm of ethylchloroformate was added stirred for about 30 minutes and then 2 gm of 4-{4-[(5S)-5-(amino methyl)-2-oxo-1,3-oxazolidin-3-yl]

phenyl}morpholin-3-one hydrochloride was added and stirred overnight at about −5° C. to −10° C. The reaction mass was then quenched with water and the organic layer was washed with 5% HCl solution and 5% sodium bicarbonate solution, followed by saturated sodium chloride solution. The organic layer was dried over sodium sulphate, distilled and degassed to yield titled compound.

Example 17: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 31 gm of 5-chloro-N-({(5S)-2-oxo-3-[4-(3-oxomorpholin-4-yl)phenyl]-1,3-oxazolidin-5-yl}methyl)thiophene-2-carboxamide, 2635 ml of acetonitrile were charged. The reaction mass was refluxed and to this 30 ml of dimethyl formamide (DMF) was added and stirred for about 30 minutes and cooled to room temperature. The reaction mixture further cooled to about 0° C.-5° C., stirred for about 2 hours, filtered, washed with cold acetonitrile and dried in air oven at about 50° C.-55° C. to yield 25 gm of titled compound.

Example 18: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 5 gm of 5-chloro-N-({(5S)-2-oxo-3-[4-(3-oxomorpholin-4-yl)phenyl]-1,3-oxazolidin-5-yl}methyl)thiophene-2-carboxamide and mixture of methanol and chloroform (1:1) were charged and refluxed for about one hour. Obtained clear solution was cooled to room temperature (RT) and stirred overnight at room temperature, filtered, washed with mixture of methanol and chloroform, dried in air oven at about 50° C.-55° C. to yield titled compound.

Example 19: Preparation of (2-[(2R)-2-hydroxy-3-{[4-(3-oxomorpholin-4-yl)phenyl]amino}propyl]-1H-isoindole-1,3(2H)-dione (Formula V)

In a clean round bottom flask, 100 gm of 4-(4-aminophenyl) morpholin-3-one, 105.7 gm of 2-[(2S)-oxiran-2-ylm-ethyl]-1H-isoindole-1,3(2H)-drone and 2 liter water were charged. The reaction mixture was heated to a temperature of about 55-60° C. and maintained for about 15 hours. 300 ml of methanol was added to reaction mass and maintained for about 3 hours at about 55-60° C., filtered, washed with water and dried in air oven at about 50° C.-60° C. to yield 175 gm of titled compound. HPLC purity: 94%.

Example 20: Preparation of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 100 gm of 2-[(2S)-2-hydroxy-3-{[4-(3-oxomorpholin-4-yl)phenyl] amino}propyl]-1H-isoindole-1,3(2H)-dione, 5 gm of 4-dimethyl amino pyridine, 82 gm of 1,1'-carbonyl diimidazole (CDI) and 1 liter of toluene were charged. The reaction mixture was heated to a temperature of about 50-60° C. and stirred for about 12 hours. The reaction mass was cooled to about 25° C.-30° C., filtered and washed with toluene. 1 liter of purified water was added to obtained cake and stirred for about 1 hour, filtered, washed with water and dried in air oven at about 50° C.-60° C. to yield 86 gm of titled compound.

Example 21: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 100 gm of 2-[(2S)-2-hydroxy-3-{[4-(3-oxomorpholin-4-yl)phenyl] amino}propyl]-1H-isoindole-1,3(2H)-dione and 800 ml of nitrobenzene were charged. Reaction mass was heated to about 80° C.-95° C., stirred for about 30 minutes and cool to about 60° C.-65° C. 1000 ml of methanol was added slowly to reaction mass and cooled to about 25° C.-30° C. and further cooled to about 0° C.-5° C. The reaction mass was stirred for about 2 hours at same temperature, filtered, washed with chilled methanol and dried in air oven at about 50° C.-60° C. to yield 86 gm of titled compound.

Example 22: Preparation of (4-{4-[(5S)-5-(amino methyl)-2-oxo-1,3-oxazolidin-3-yl] phenyl}morpholin-3-one hydrochloride (Formula IIa)

In a clean round bottom flask, 100 gm of (2-({(5S)-2-oxo-3-[4-(3-oxomorpholin-4-yl)phenyl]-1,3-oxazolidin-5-yl}methyl)-1H-isoindole-1,3(2H)-dione), 1500 ml of methylene dichloride (MDC) and 239.5 gm of 40% aq. methyl amine solution were charged at room temperature. The reaction mixture was heated to a temperature of about 35° C.-45° C. for about 15 hours and cooled to about 25° C.-30° C. Layer was separated and MDC layer distilled off under vacuum. 500 ml of methanol was added to reaction mass and heated to about 40° C.-45° C. for dissolution and then 20 ml of 35% HCL solution was added till pH 1-3. The slurry was stirred for about 30 minutes, cooled, filtered, washed with methanol and dried in air oven at about 50° C.-55° C. to yield 58 gm of titled compound.

Example 23: Preparation of 2-[(2S)-oxiran-2-ylmethyl]-1H-isoindole-1,3(2H)-dione (Formula VII)

In a clean round bottom flask, 5 gm of phthalimide, 7.85 gm of S-epichlorohydrin, 6.9 gm sodium acetate and 50 ml of isopropyl alcohol were charged. The reaction mass was heated to about 65° C.-70° C. and maintained for about 24 hours to about 30 hours. The reaction mass was cooled to about 25° C. and concentrated under reduced pressure at below 40° C. then 50 ml of toluene was added and stirred for about 30 minutes and filtered. To obtained filtrate 17.76 gm of potassium carbonate was added and reaction mass was heated to about 100° C.-110° C. and maintained for about 3 hours to about 5 hours at same temperature. The reaction mass was cooled to about 25° C., filtered and concentrated and degassed. 50 ml of cyclohexane was added to reaction mass and stirred for about 30 minutes, filtered and dried under reduced pressure at about 50-55° C. to yield titled compound as oil (5 gm)

Example 24: Preparation of 5-chloro thiophene-2-carboxaldehyde (Formula VIII)

In a clean round bottom flask, 19.38 gm of phosphorous oxychloride, 5 gm of 2-Chloro thiophene were charged and reaction mass was heated to about 50° C.-55° C. 9.244 gm of dimethyl formamide (DMF) was added to reaction mass at same temperature and cooled to about 0° C.-5° C. 10% sodium hydroxide solution was added to reaction mass & extracted with methylene dichloride then obtained organic layer washed with water followed by sodium chloride solution. The organic layer distilled off & degassed under vacuum below 45° C. to yield titled compound as oily mass. HPLC purity: 98%.

Example 25: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl]phenyl}morpholin-3-one hydrochloride, 6 ml of acetonitrile, 0.026 gm of silver iodate, 0.017 gm copper iodide, 0.82 gm of calcium carbonate and 1.3 gm of 70% tertiary butyl hydro peroxide were charged and stirred for about 10 minutes then reaction mixture was heated to about 40° C.-45° C. 2 gm of 5-chloro thiophene-2-carboxaldehyde was added at about 40° C.-45° C. and maintained the reaction for about 6 to about 7 hours. After completed the reaction (checked by TLC) 20 ml of dimethyl formamide (DMF) was added and reaction mass was heated to about 70-75° C., filtered and washed with DMF. To be obtained filtrate water was added drop wise at about 0° C.-10° C., stirred for about 3-4 hours and filtered to yield 3 gm of titled compound.

Example 26: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl]phenyl}morpholin-3-one hydrochloride, 6 ml of acetonitrile, 0.026 gm of silver iodate, 0.017 gm copper iodide, 0.82 gm of calcium carbonate were charged and stirred for about 10 minutes then reaction mixture was heated to about 40° C.-45° C. 2 gm of 5-chloro thiophene-2-carboxaldehyde was added to reaction mixture at about 40° C.-45° C. then 1.3 gm of 70% tertiary butyl hydro peroxide was charged to reaction mixture and maintained the reaction for about 6 to about 7 hours. After completed the reaction (checked by TLC) 20 ml of dimethyl formamide (DMF) was added and reaction mass was heated to about 70-75° C., filtered and washed with DMF. To the obtained filtrate, water was added drop wise at about 0° C.-10° C., stirred for about 3-4 hours and filtered to yield 3 gm of titled compound.

Example 27: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl]phenyl}morpholin-3-one hydrochloride, 6 ml of acetonitrile, 0.026 gm of silver iodate, 0.017 gm copper iodide, 1 gm of sodium bicarbonate and 1.3 gm of 70% tertiary butyl hydro peroxide were charged and stirred for about 10 minutes then reaction mixture was heated to about 40° C.-45° C. 2 gm of 5-chloro thiophene-2-carboxaldehyde was added at about 40° C.-45° C. and maintained the reaction for about 6 to about 7 hours. After completed the reaction (checked by TLC) 20 ml of dimethyl formamide (DMF) was added and reaction mass was heated to about 70-75° C., filtered and washed with DMF. To be obtained filtrate water was added drop wise at about 0° C.-10° C., stirred for about 3-4 hours and filtered to yield 1 gm of titled compound.

Example 28: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl]phenyl}morpholin-3-one hydrochloride, 6 ml of acetonitrile, 0.026 gm of silver iodate, 0.017 gm copper iodide, 1.2 gm of potassium carbonate and 1.3 gm of 70% tertiary butyl hydro peroxide were charged and stirred for about 10 minutes then reaction mixture was heated to about 40° C.-45° C. 2 gm of 5-chloro thiophene-2-carboxaldehyde was added at about 40° C.-45° C. and maintained the reaction for about 6 to about 7 hours. After completed the reaction (checked by TLC) 20 ml of dimethyl formamide (DMF) was added and reaction mass was heated to about 70-75° C., filtered and washed with DMF. To be obtained filtrate water was added drop wise at about 0° C.-10° C., stirred for about 3-4 hours and filtered to yield 1 gm of titled compound.

Example 29: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl]phenyl}morpholin-3-one hydrochloride, 6 ml of ethyl acetate, 0.026 gm of silver iodide, 0.017 gm copper iodide, 1 gm of sodium bicarbonate and 1.3 gm of 70% tertiary butyl hydro peroxide were charged and stirred for about 10 minutes then reaction mixture was heated to about 40° C.-45° C. 2 gm of 5-chloro thiophene-2-carboxaldehyde was added at about 40° C.-45° C. and maintained the reaction for about 6 to about 7 hours. After completed the reaction (checked by TLC) 20 ml of dimethyl formamide (DMF) was added and reaction mass was heated to about 70-75° C., filtered and washed with DMF. To be obtained filtrate water was added drop wise at about 0° C.-10° C., stirred for about 3-4 hours and filtered to yield 1.5 gm of titled compound.

Example 30: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in 20 ml acetic acid at reflux. 20 ml of water was added to reaction mass, cooled to about room temperature and maintained for about 3 to about 5 hours, filtered and washed with water to yield pure titled compound.

Example 31: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in a mixture of methanol (40 ml) and MDC (60 ml) at reflux. Charcoal was added to reaction mass and filtered on hyflo. The obtained filtrate was cooled to 25-30° C. and maintained for about 3-5 hours, filtered, washed with methanol to yield pure titled compound.

Example 32: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in a mixture of methanol (40 ml) and MDC (60 ml) at reflux. After dissolution solvent was distilled out the solvent under vacuum till 50 ml, cooled to about 25-30° C. and maintained for about 3 hours to about 5 hours, filtered and washed with methanol to yield pure titled compound.

Example 33: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in a mixture of methanol (40 ml) and MDC (60 ml) at reflux. After dissolution solvent was distilled out the solvent under vacuum till 50 ml, cooled to about 0-5° C. and maintained for about 5 hours to about 7 hours, filtered and washed with methanol to yield pure titled compound.

Example 34: Preparation of (2-[(2R)-2-hydroxy-3-{[4-(3-oxomorpholin-4-yl)phenyl]amino}propyl]-1H-isoindole-1,3(2H)-dione (Formula V)

In a clean round bottom flask, 100 gm of 4-(4-aminophenyl) morpholin-3-one, 126.9 gm of 2-[(2S)-oxiran-2-ylmethyl]-1H-isoindole-1,3(2H)-drone, 1.5 liter water and 100 ml methanol were charged. The reaction mixture was heated to a temperature of about 55-60° C. and maintained for about 15 hours. The reaction mass was cooled to about room temperature and stirred for about one hour, filtered, washed with water and dried in air oven at about 50° C.-60° C. to yield 174 gm of titled compound.

Example 35: Preparation of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 100 gm of 2-[(2S)-2-hydroxy-3-{[4-(3-oxomorpholin-4-yl)phenyl]amino}propyl]-1H-isoindole-1,3(2H)-dione, 5 gm of 4-dimethyl amino pyridine, 82 gm of 1,1'-carbonyl diimidazole (CDI) and 1.5 liter of toluene were charged. The reaction mixture was heated to about 50-55° C. and stirred for about 12 hours. A second lot of 82 gm of 1,1-carbonyl diimidazole (CDI) was charged and the reaction mass was maintained for about 12 hours. The reaction mass was then cooled to about 0° C.-5° C. and stirred for about 2 hours, filtered, washed with chilled toluene and dried in air oven at about 50° C.-60° C. to yield 90 gm of titled compound.

Example 36: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 100 gm of 2-[(2S)-2-hydroxy-3-{[4-(3-oxomorpholin-4-yl)phenyl]amino}propyl]-1H-isoindole-1,3(2H)-dione and 700 ml of nitrobenzene and 1000 ml methanol were charged. Reaction mass was heated to about 85-90° C., cooled to about 25-30° C., stirred for about 120 minutes and filtered, washed with methanol and dried in vacuum oven at about 50° C.-60° C. to yield 86 gm of titled compound.

Example 37: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 2 gm of 2-[(2S)-2-hydroxy-3-{[4-(3-oxomorpholin-4-yl)phenyl]amino}propyl]-1H-isoindole-1,3(2H)-dione and 16 ml of acetonitrile and 4 ml acetone were charged. Reaction mass was heated to about 50-55° C., cooled to about 25-30° C., stirred for about 120 minutes and filtered, washed with acetonitrile and dried in vacuum oven at about 50° C.-60° C. to yield 1.7 gm of titled compound.

Example 38: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 2 gm of 2-[(2S)-2-hydroxy-3-{[4-(3-oxomorpholin-4-yl)phenyl]amino}propyl]-1H-isoindole-1,3(2H)-dione and 20 ml of water and 4 ml DMF were charged. Reaction mass was heated to about 70-75° C., stirred for about 120 minutes and filtered, washed with water and dried in vacuum oven at about 50° C.-60° C. to yield 1.6 gm of titled compound.

Example 39: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 2 gm of 2-[(2S)-2-hydroxy-3-{[4-(3-oxomorpholin-4-yl)phenyl]amino}propyl]-1H-isoindole-1,3(2H)-dione and 10 ml of THF. Reaction mass was heated to about 65-70° C., stirred for about 120 minutes, cool to RT and filtered, washed with THF and dried in vacuum oven at about 50° C.-60° C. to yield 1.6 gm of titled compound.

Example 40: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 2 gm of 2-[(2S)-2-hydroxy-3-{[4-(3-oxomorpholin-4-yl)phenyl]amino}propyl]-1H-isoindole-1,3(2H)-dione and 10 ml of acetonitrile. Reaction mass was heated to about 65-70° C., stirred for about 120 minutes, cool to RT and filtered, washed with acetonitrile and dried in vacuum oven at about 50° C.-60° C. to yield 1.5 gm of titled compound.

Example 41: Purification of (2-({(5S)-2-oxo-3-[4-(3-oxomorpholin-4-yl)phenyl]-1,3-oxazolidin-5-yl}methyl)-1H-isoindole-1,3(2H)-dione (Formula IV)

In a clean round bottom flask, 2 gm of 2-[(2S)-2-hydroxy-3-{[4-(3-oxomorpholin-4-yl)phenyl]amino}propyl]-1H-isoindole-1,3(2H)-dione, 16 ml of acetonitrile and 4 ml cyclohexane. Reaction mass was heated to about 65-70° C., stirred for about 120 minutes, cool to room temperature (RT) and filtered, washed with acetonitrile and dried in vacuum oven at about 50° C.-60° C. to yield 1.7 gm of titled compound.

Example 42: Preparation of (4-{4-[(5S)-5-(amino methyl)-2-oxo-1,3-oxazolidin-3-yl] phenyl}morpholin-3-one hydrochloride (Formula IIa)

In a clean round bottom flask, 100 gm of (2-({(5S)-2-oxo-3-[4-(3-oxomorpholin-4-yl)phenyl]-1,3-oxazolidin-5-yl}methyl)-1H-isoindole-1,3(2H)-dione, 1500 ml of methanol and 239.5 gm of 40% aq. methyl amine solution were charged at room temperature. The reaction mixture was heated to a temperature of about 36-45° C. for about 15 hours and cooled to about 25° C.-30° C. IPA-HCl solution was added till pH 1-3. The slurry was stirred for about 30 minutes, cooled, filtered, washed with methanol and dried in air oven at about 50° C.-55° C. to yield 55 gm of titled compound. HPLC purity: 99.30%.

Comparative Example 43: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 4.4 gm of 4-{4-[(5S)-5-(amino methyl)-2-oxo-1,3-oxazolidin-3-yl] phenyl}morpholin-3-one hydrochloride, 5.2 ml of acetonitrile, 0.025 gm of silver iodate, 0.017 gm copper iodide and 0.8 gm of calcium carbonate and stirred for about 10 minutes. 2 gm of 5-chloro thiophene-2-carboxaldehyde was added at about 25-30° C. Then, 1.3 gm of 70% tertiary butyl hydro peroxide was added. The reaction mixture was heated to about 40-50° C. and maintained for 6 hours at same temperature. After completed the reaction ethyl acetate and HCl was added, filtered and washed with ethyl acetate and dried in air oven at about 50-60° C. to yield 2.1 gm of titled compound. HPLC purity: 70.46%.

Example 44: Preparation of 5-chloro-N-({(5S)-2-oxo-3-[4-(3-oxomorpholin-4-yl)phenyl]-1,3-oxazolidin-5-yl}methyl)thiophene-2-carboxamide (Formula I)

In a clean round bottom flask, 3 gm of 4-{4-[(5S)-5-(amino methyl)-2-oxo-1,3-oxazolidin-3-yl] phenyl}morpholin-3-one hydrochloride (Formula IIa), 6 ml of acetonitrile, 0.026 gm of silver iodate, 0.0087 gm copper iodide, 0.82 gm of calcium carbonate and 1.3 gm of 70% tertiary butyl hydro peroxide were charged and stirred for about 10 minutes then 2 gm of 5-chloro thiophene-2-carboxaldehyde (Formula VIII) was added at about 25-30° C. The reaction mixture was heated to about 40-50° C. and maintained for about 6 to about 8 hours at same temperature. After completed the reaction ethyl acetate and HCl was added, filtered and washed with ethyl acetate and dried. To obtained compound, formic acid was added and heated to about 40-50° C. and then washed with toluene. To the formic acid layer, water was added, filtered, washed with water and dried. To the dried compound, dimethyl formamide (DMF) was added and heated to about 70-80° C. and filtered. DMF solution is then passed through neutral alumina column and to eluted DMF solution, water was added, filtered, washed with water and died in air oven at about 50-60° C. to yield 2.2 gm of titled compound. HPLC purity: 99.5%.

The reaction was periodically monitored by HPLC, starting from zero hour and then every 15 minute up to one hour and thereafter every hour till 12 hour time period. The HPLC data generated demonstrates that reaction pathway proceeds through oxidative amidation to directly give rivaroxaban and does not proceed via intermediate compound of formula XI, as is seen by the insignificant level of compound XI in the below table. The data shows that initially at 15 minute more than 60% of rivaroxaban is formed and compound of formula XI does not exceed more than 0.27% at any time throughout the 12 hours monitoring of the reaction mixture.

| Reaction monitoring for % compound of formula XI | | | |
| --- | --- | --- | --- |
| Time | % Compound IIa | % Rivaroxaban | % Compound XI |
| 0 hr | 6.08 | 60.31 | 0.27 |
| 15 min | 2.43 | 62.59 | 0.06 |
| 30 min | 1.64 | 62.59 | 0.06 |
| 45 min | 2.22 | 65.75 | 0.05 |
| 1 hour | 1.56 | 71.65 | 0.16 |
| 2 hour | 1.1 | 75.87 | 0.13 |
| 3 hour | 0.62 | 77.19 | 0.04 |
| 4 hour | 0.62 | 74.05 | 0.07 |
| 5 hour | 0.7 | 75.21 | 0.09 |
| 6 hour | 0.64 | 75.19 | 0.08 |
| 7 hour | 0.64 | 75.82 | 0.1 |
| 8 hour | 0.51 | 71.37 | 0.15 |
| 9 hour | 0.49 | 73.2 | 0.14 |
| 10 hour | 0.98 | 72.91 | 0.12 |
| 11 hour | 0.9 | 74.16 | 0.13 |
| 12 hour | 0.79 | 73.88 | 0.13 |
| Isolated solid (Rivaroxaban) | 0.05 | 93.51 | 0.05 |

Example 45: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in a mixture of methanol (40 ml) and MDC (60 ml) at reflux. After dissolution solvent was distilled out atmospherically till 30 ml, cooled to about 25-30° C. and maintained for about 1 hour to about 2 hours, filtered and washed with methanol to yield pure titled compound. HPLC purity: 99.7%; Chiral HPLC purity: 99.99%; Bulk density: 0.31 gm/cm$^3$; Tap density: 0.47 gm/cm$^3$; surface area: 0.32 m$^2$/gm; Particle size distribution: $d_{10}$ about 14 microns, $d_{50}$ about 37 microns and $d_{90}$ about 75 microns; Particle size distribution after micronization: $d_{10}$ about 6 microns, $d_{50}$ about 28 microns and $d_{90}$ about 70 microns.

Example 46: Purification of 5-chloro-N-({(5S)-2-oxo-3-[4-(3-oxomorpholin-4-yl)phenyl]-1,3-oxazolidin-5-yl}methyl)thiophene-2-carboxamide In a clean round bottom flask, 2 gm of 5-chloro-N-({(5S)-2-oxo-3-[4-(3-oxomorpholin-4-yl)phenyl]-1,3-oxazolidin-5-yl}methyl)thiophene-2-carboxamide was dissolved in a mixture of methanol (40 ml) and MDC (60 ml) at reflux. After dissolution solvent was distilled out atmospherically till 30 ml, cooled to about 25-30° C. and maintained for about 1 hour to about 2 hours, filtered and washed with methanol-MDC (1:1) mixture to yield pure titled compound. HPLC purity: 99.7% and Chiral HPLC purity: 99.99%.

We claim:

1. A process for the preparation of rivaroxaban, a compound of Formula I,

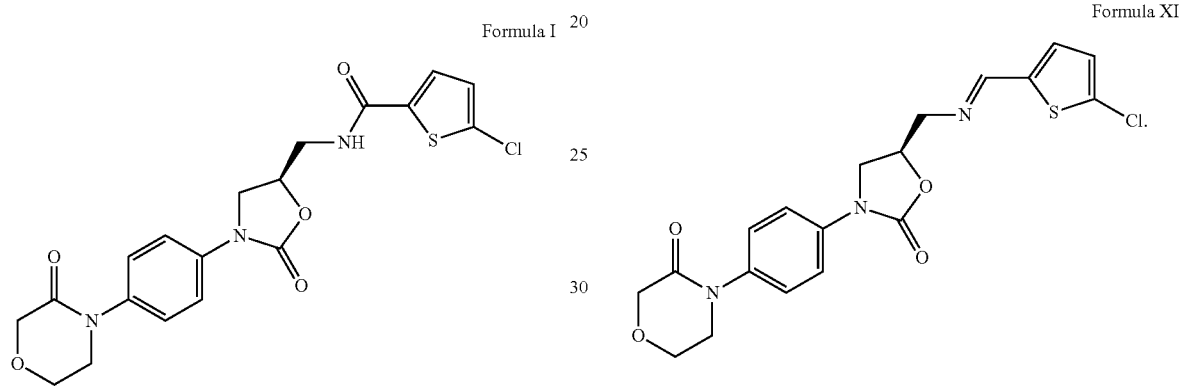

Formula I comprising the steps of
a) contacting a compound of Formula II or salt thereof

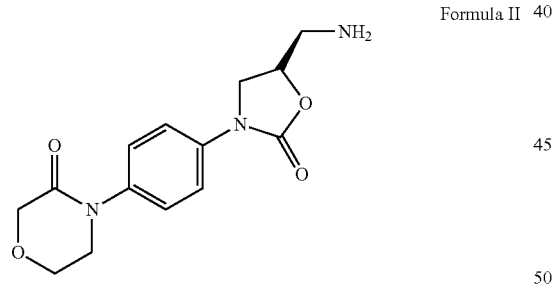

Formula II with an oxidizing agent to form a first reaction mixture;
b) contacting the first reaction mixture with a compound of formula VIII,

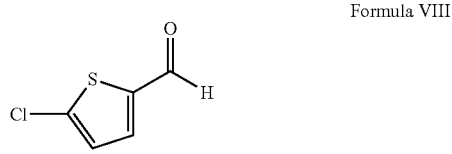

Formula VIII to form a second reaction mixture; and
c) isolating a compound of formula I from the second reaction mixture.

2. The process as claimed in claim 1, wherein the oxidizing agent is selected from the group consisting of tert-butyl hydroperoxide, benzoyl peroxide and cumene hydro peroxide.

3. The process as claimed in claim 2, wherein the oxidizing agent is tert-butyl hydroperoxide.

4. The process as claimed in claim 1, wherein the amount of the oxidizing agent is from about 1 mole to about 3 moles per mole of the compound of formula II or salt thereof.

5. The process as claimed in claim 1, wherein the contacting step (b) is carried out at about 25° C. to about 50° C.

6. The process as claimed in claim 1, wherein the reaction is carried out at about 5° C. to about 80° C.

7. The process as claimed in claim 1, wherein rivaroxaban, a compound of Formula I, is free of compound of formula XI

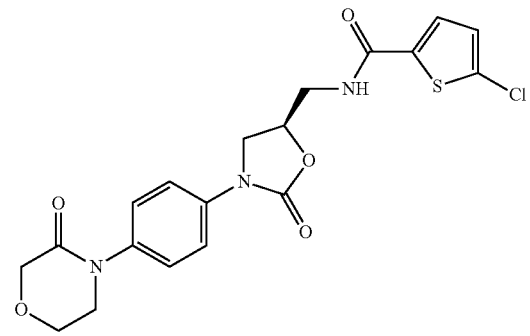

Formula XI

8. The process for purifying rivaroxaban, a compound of Formula I, as prepared in claim 1, comprising:
a) providing a solution of rivaroxaban in a mixture of an alcohol solvent and a halogenated hydrocarbon solvent or their aqueous mixtures;
b) precipitating the solid from the solution; and
c) isolating the pure rivaroxaban, a compound of Formula I.

9. The process as claimed in claim 8, wherein the alcoholic solvent is methanol.

10. The process as claimed in claim 8, wherein the halogenated hydrocarbon solvents dichloromethane.

11. Rivaroxaban, a compound of Formula I,

Formula I containing less than about 0.15% w/w as measured by HPLC of the compound of formula XI Formula XI
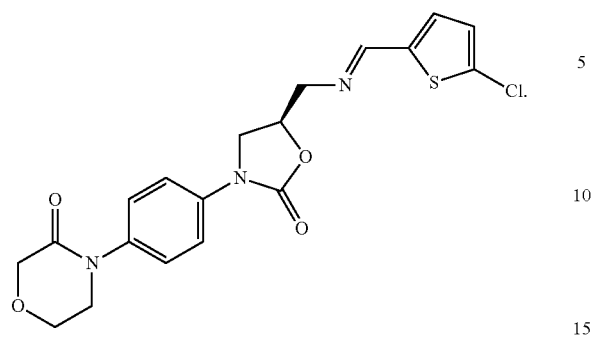
* * * * *